US008851292B2

(12) United States Patent
Meyer et al.

(10) Patent No.: US 8,851,292 B2
(45) Date of Patent: Oct. 7, 2014

(54) PACKAGING SYSTEM FOR SHIPPING, STORING, DISPLAYING, AND/OR DISPENSING ABSORBENT ARTICLES

(75) Inventors: Kevin Jon Meyer, Minster, OH (US); Jeffrey Karim, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 334 days.

(21) Appl. No.: 12/823,553

(22) Filed: Jun. 25, 2010

(65) Prior Publication Data
US 2011/0315585 A1 Dec. 29, 2011

(51) Int. Cl.
*B65D 5/50* (2006.01)
*B65D 5/52* (2006.01)
*A61F 13/551* (2006.01)
*B65D 5/16* (2006.01)
*B65D 77/02* (2006.01)
*B65D 5/10* (2006.01)
*B65D 5/02* (2006.01)

(52) U.S. Cl.
CPC ............ *A61F 13/5511* (2013.01); *B65D 5/16* (2013.01); *B65D 77/02* (2013.01); *B65D 5/103* (2013.01); *B65D 5/029* (2013.01)
USPC ............ 206/769; 206/736; 206/440; 229/100

(58) Field of Classification Search
USPC .......... 206/440, 736–774, 824; 229/107–108, 229/117.31, 117.27, 104, 200, 209, 216, 229/240, 100
See application file for complete search history.

(56) References Cited

U.S. PATENT DOCUMENTS

| | | | |
|---|---|---|---|
| 3,894,681 A * | 7/1975 | Arneson et al. | 206/141 |
| 4,883,675 A | 11/1989 | Wernz | |
| 4,934,535 A | 6/1990 | Muckenfuhs et al. | |
| 4,966,286 A | 10/1990 | Muckenfuhs | |
| 4,967,909 A | 11/1990 | McKibben | |
| 5,022,216 A | 6/1991 | Muckenfuhs et al. | |
| 5,605,279 A | 2/1997 | Adamek | |
| 5,685,479 A | 11/1997 | Weber-Caspers | |
| 5,967,665 A | 10/1999 | MacDonald et al. | |
| 6,209,786 B1 * | 4/2001 | Yelton et al. | 229/241 |
| 6,715,639 B2 | 4/2004 | Spivey | |
| 7,021,466 B2 | 4/2006 | Kuske et al. | |
| 7,175,047 B2 * | 2/2007 | Spivey | 221/305 |

(Continued)

FOREIGN PATENT DOCUMENTS

| | | |
|---|---|---|
| EP | 1533239 A2 | 5/2005 |
| EP | 1386846 B1 | 8/2006 |

OTHER PUBLICATIONS

Photographs of Pampers package sold at Target in May-Jul. 2010.

(Continued)

*Primary Examiner* — Mickey Yu
*Assistant Examiner* — Chun Cheung
(74) *Attorney, Agent, or Firm* — Andrew A. Paul; Laura L. Whitmer; Sarah M. DeCristofaro (57) ABSTRACT

A blank having panels and flaps, a carton foldably constructed from the blank, a polybag, and a packaging system that includes the carton, the polybag, or both. The packaging systems include, among other things, certain tabs, flaps, cut out, and tear lines that allow absorbent articles contained in the several systems to be easily viewed and removed, while maintaining sufficient integrity of the packaging system.

25 Claims, 4 Drawing Sheets

(56) References Cited

U.S. PATENT DOCUMENTS

| | | |
|---|---|---|
| 7,780,006 B2 | 8/2010 | Clark, Jr. et al. |
| 2006/0006096 A1* | 1/2006 | Funk .............................. 206/746 |
| 2006/0124494 A1 | 6/2006 | Clark, Jr. et al. |
| 2006/0131197 A1 | 6/2006 | Price |
| 2006/0131200 A1 | 6/2006 | Boldra et al. |
| 2007/0151887 A1 | 7/2007 | Clark, Jr. et al. |
| 2008/0073420 A1 | 3/2008 | Walling et al. |
| 2010/0019022 A1 | 1/2010 | Ryan et al. |
| 2010/0230432 A1 | 9/2010 | Cardinal et al. |
| 2010/0282637 A1 | 11/2010 | Clark, Jr. et al. |
| 2011/0162998 A1* | 7/2011 | Wurth et al. .................. 206/769 |

OTHER PUBLICATIONS

Photographs of Pampers diapers and package available for purchase beginning Jun. 2008.

\* cited by examiner

PACKAGING SYSTEM FOR SHIPPING, STORING, DISPLAYING, AND/OR DISPENSING ABSORBENT ARTICLES

FIELD OF THE INVENTION

In one aspect, the invention relates generally to a partially closed carton and a polybag, each capable of containing absorbent articles, e.g. diapers, and which alone or in combination comprise a packaging system having unique features that allow the absorbent articles to be shipped, stored, displayed, and/or dispensed without destroying the overall structural integrity of the system.

BACKGROUND OF THE INVENTION

Fully closed cartons capable of containing absorbent articles are presently used. Typically, the absorbent articles are packaged in primary packaging, e.g. polybags, which are then placed into secondary packaging, e.g. cardboard boxes. The manufacturer may provide printed indicia on either or both of the primary packaging and secondary packaging, depending on which is intended to be the product ultimately purchased by a consumer. The cardboard box may be shipped eventually to a retailer and placed on shelf, then a consumer purchases the box, takes it home, and then opens the box and disposes of it. Alternately, the consumer may purchase the box via e-commerce, e.g. online through the internet, and the box is shipped directly to the consumer. In yet another alternative, the retailer may open the box and place polybagged absorbent articles on shelf for sale, and likely stack them to save space and/or to create a display. After the taking the product home, the consumer typically opens the box, if any, and then opens the polybag containing the absorbent articles, removes all or some of the absorbent articles and then places them in yet another container, e.g. a diaper bag or similar container attached or placed proximately to a changing table, from which they are retrieved at the point of use.

Many of these aforementioned cartons suffer from one or more disadvantages. For example, absorbent articles contained in plastic film bags, e.g. made of polyethylene, commonly known as "polybags", may suffer deformation by the time they arrive at store or home given that many polybags may be stacked or otherwise arranged on top of each other during shipping or display, or other items being simultaneously shipped or displayed may be placed on top of otherwise situated such that the weight of the other items causes deformation of the absorbent articles. Once in store, polybags may be unstable on shelf in a similar manner, e.g. they are susceptible to falling over or being placed by a stockperson at an angle relative to a viewing consumer where the orientation of the polybag does not allow the consumer to readily see and understand the indicia on the polybag, e.g. a viewing consumer may see a group of polybags together in a store display where some of them are top-end up, while others are side-end up, and some are even upside down. Also, the polybags may be deformed by other polybags or other items on shelf. If the polybag is kept in the box while on display, then the consumer cannot see the actual product and must rely on indicia provided on the box, if any, to relay an image of the actual product to the consumer, which many consumers may find insufficient. Further, once the polybag is taken home by a consumer, the consumer may find it difficult to store unused absorbent articles in the polybag and/or to retrieve a single absorbent article from the polybag once it has been torn open. Further yet, with polybags that have tear strips located very near, if not at the end of a row of absorbent articles packed within the polybag, the indicia is printed on the polybag such that the end of the row is at the top of the polybag when the indicia is viewed upright, thus causing a consumer to either suffer the inconvenience of removing absorbent articles from the side of the polybag in order to view the indicia in an upright position, or suffer the inconvenience of viewing the indicia oriented at a right angle to the upright position in order to conveniently remove absorbent articles from what becomes the top of the polybag as the polybag stands upright in this orientation. In effect, many of these containers lack sufficient integrity once they have been opened, do not provide visibility of the product, are not designed to have the indicia printed on the container continue to be oriented for easy viewing and understanding after the container is opened, or combinations thereof.

SUMMARY OF THE INVENTION

In one aspect, the invention relates to a blank having panels and flaps, a carton foldably constructed from the blank, a polybag, and a packaging system that comprises the carton, the polybag, or both. The packaging systems comprise, among other things, certain tabs, flaps, cut out, and tear lines that allow absorbent articles contained in the several systems to be easily viewed and removed, while maintaining sufficient integrity of the packaging system.

It is an object of this invention to provide a packaging system that preserves the integrity of the system during shipping, storing, displaying, and/or dispensing. It is another object of this invention to provide a packaging system that is stable and allows stacking. It is another object of this invention to provide a packaging system that improves the visibility of actual product to the consumer when displayed. It is another object of this invention to provide a packaging system that intuitively communicates to a stock person how to arrange the product in store displays so as to improve consumer readability and understanding of indicia printed on the packaging system, and to enjoy a more aesthetically pleasing store display that is orderly arranged. It is another object of this invention to provide a packaging system that provides improved dispensing of absorbent articles from the system. It is another object of this invention to provide a packaging system that uses less material than conventional systems thereby being friendly to the environment. These and other objects, features, and advantages of the present invention will become more apparent upon reading the following specification in conjunction with the accompanying drawing figures.

DETAILED DESCRIPTION OF THE INVENTION

The present invention is intended primarily for use with absorbent articles. As used herein, the term "absorbent article" refers to devices which absorb and contain body exudates, and, more specifically, refers to devices which are placed against or in proximity to the body of the wearer to absorb and contain the various exudates discharged from the body. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

In an embodiment of the invention, a packaging system comprises the carton described herein, made from the blank described herein. In another embodiment, a packaging system comprises the polybag described herein. In yet another embodiment, a packaging system comprises a polybag being placed within such carton, preferably the polybag described herein.

Figure 1:
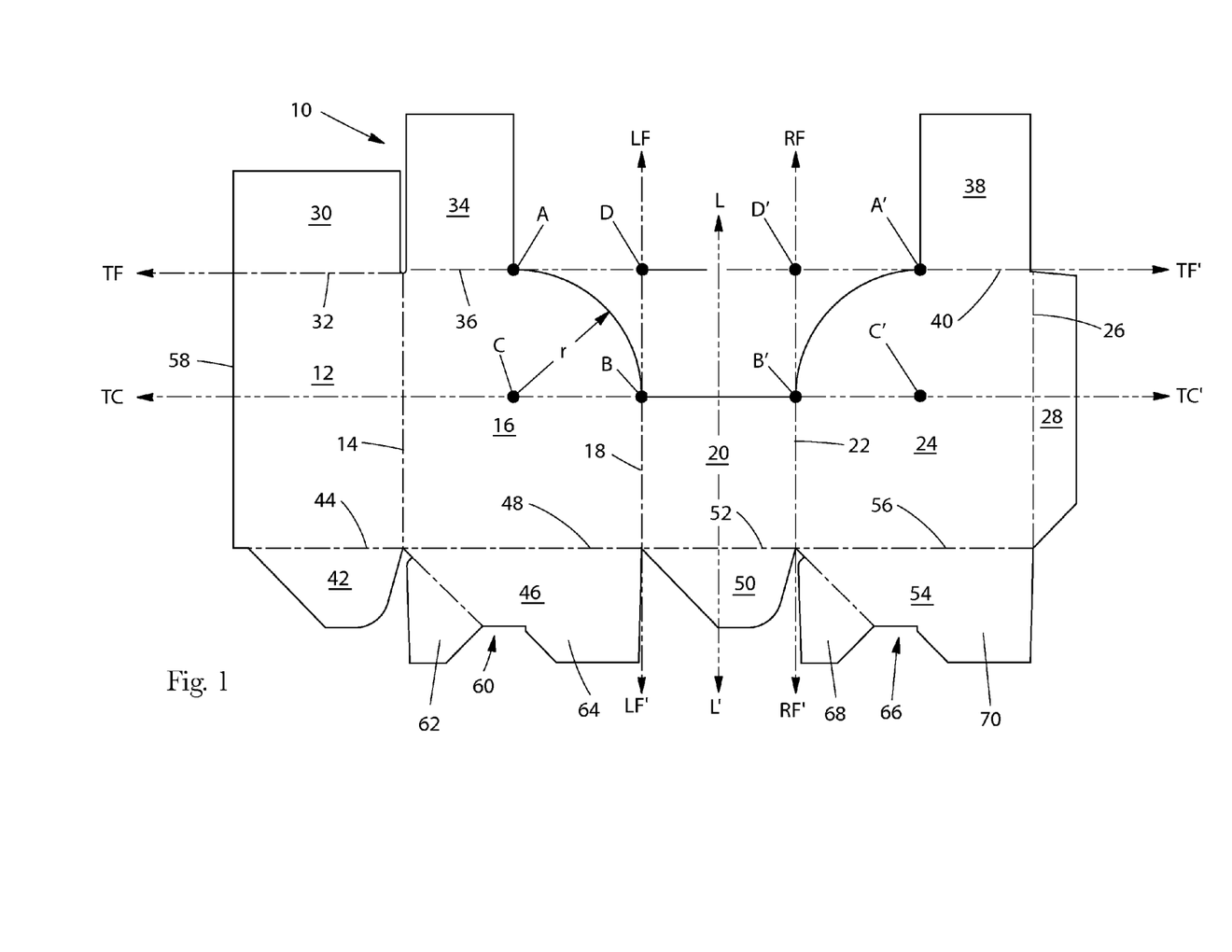
FIG. 1 is a plan view of a blank from which a carton according to this invention is formed.

As shown in FIG. 1, a blank 10 is formed from a foldable sheet material, e.g. paperboard, cardboard (corrugated or not), or boxboard. The blank 10 has a back panel 12 which is connected by fold line 14 to side panel 16, which in turn is connected by fold line 18 to front panel 20. Front panel 20 is connected by fold line 22 to side panel 24, which in turn is connected by fold line 26 to back flap 28. Back panel 12 has a back edge 58.

The portion of the blank that will form a partially closed end of the carton has a back end flap 30 connected to back panel 12 by fold line 32. Top panel 34 is connected to side panel 16 by fold line 36. Side end flap 38 is connected to side panel 24 by fold line 40. In another embodiment (not shown), top panel 34 is provided with a member to recloseably attach top panel 34 to side end flap 38. Such member may include, e.g., placing one mate of a hook and loop fastening system on the surface of top panel 34 that will contact a surface of side end flap 38, and placing the other mate of such a system on side end flap 38. Another example is providing top panel 34 with a slot tab along the edge of top panel 34 that is opposite fold line 36, and a corresponding slot is provided along fold line 40 to releasably receive the slot tab.

The portion of the blank that will form a closed end of the carton has a back end flap 42 connected to back panel 12 by fold line 44, side end flap 46 is connected to side panel 16 by fold line 48, front end flap 50 is connected to front panel 20 by fold line 52, and side end flap 54 is connected to side panel 24 by fold line 56. In an embodiment, side end flap 46 and side end flap 54 are provided with notches 60 and 66, respectively, which delineate tabs 62 and 64, and tabs 68 and 70, respectively, which may be useful in securing side end flap 46 and side end flap 54 to each other when the carton is assembled, thereby improving the structural integrity of the carton.

It will be understood by those skilled in the art that side panel 16 and side panel 24 of the carton of the present invention are generally symmetrical about a vertical line of bisection L-L' drawn through front panel 20. This symmetry is believed to aid in the efficient production of the present blank, improve the rigidity of the carton to be assembled therefrom, and/or enhance the attractiveness of the assembled carton when used to display absorbent articles contained therein.

A cut out of the portion of the sheet corresponding to the polygon A-B-B'-A'-A is provided. The portion of the cut out in the front of the carton is provided such that substantially all of the area of the front panel that is within 50% or less, preferably 45% or less, more preferably 40% or less, of the distance from Line TF-TF' to fold line 52 is cut away along Line TC-TC'.

In an embodiment, substantially symmetrical cut outs of side panels 16 and 24 are provided such that substantially all of the area of each side panel defined as follows, is cut away: (i) an arc originates at Point B (or B', respectively) and terminates at a Point A (or A', respectively); and (ii) the portion of side panel 16 (or 24, respectively) that is on the side of the arc that falls within polygon A-B-B'-A'-A is the portion to be cut away. In an embodiment, a portion of the arc is concave relative to the center of side panel 16 (or 24, respectively). In another embodiment, all or substantially all of the arc is concave relative to the center of side panel 16 (or 24, respectively). In an embodiment, a portion of the arc is convex relative to the center of side panel 16 (or 24, respectively). In another embodiment, all or substantially all of the arc is convex relative to the center of side panel 16 (or 24, respectively). In yet another embodiment, the shape of the arc of side panel 16 is the same or substantially the same as the arc of side panel 24.

In another embodiment, the area cut away to form the substantially symmetrical cut outs of each of the portions of the sheet corresponding to the sides of the carton is defined as follows: (i) a Point C (or C', respectively) on Line TC-TC' is identified that is equidistant from fold line 18 (or 22, respectively); (ii) the length from the fold line to the point defines a radius r; (iii) from Point C (or C', respectively), an arc having radius r is extended from Point B (or B', respectively) to Point A (or A', respectively); and (iv) the portion of side panel 16 (or 24, respectively) on the side of the arc that falls within polygon A-B-B'-A'-A is the portion to be cut away.

In yet another embodiment, the area cut away to form the substantially symmetrical cut outs of each of the portions of the sheet corresponding to the sides of the carton is defined as follows: the origination point and termination point of the arc are equidistant from Point D (or D', respectively) on Line LF-LF' (or RF-RF', respectively); and (ii) the portion of side panel 16 (or 24, respectively) on the side of the arc that falls within polygon A-B-B'-A'-A is the portion to be cut away, as shown in FIG. 1. Preferably, for each of these embodiments for the substantially symmetrical cut outs, the point at which the arc terminates (A, or A') is also where the length $L_T$ of top panel 34 terminates, as is shown in FIG. 2.

The various panels and flaps may be of any size suitable for making a carton for shipping, storing, displaying, and/or dispensing absorbent articles, as desired. The skilled person will appreciate that care should be taken to select dimensions of each panel and flap that are complementary to dimensions of other panels and flaps, and of course, the absorbent articles. Referring to FIG. 2, some preferred dimensions selected to achieve excellent structural integrity and improved visibility of the absorbent articles are described independently of each other: preferably, the height $H_S$ of side panels 16 (shown) and 24 (not shown) is from 8 to 10 inches, the length $L_S$ of side panels 16 (shown) and 24 (not shown) is from 7 to 8 inches, the width W of front panel 20 is from 4 to 6 inches, preferably 5 inches, the height $H_F$ of front panel 20 is from 4 to 6 inches, preferably 5 inches, and the length $L_T$ of top panel 34 is from 2 to 5 inches, preferably 3 to 4 inches, more preferably 3½ inches. Preferably $H_S > L_S$. Preferably, $H_F$ is ≥0.5 $H_S$. In an embodiment, $H_F$ is ≥0.55 $H_S$. In another embodiment, $H_F$ is ≥0.6 $H_S$. Preferably, $H_F$ is ≥$L_T$. In an embodiment, the area of back panel 12 is from 1.6 to 2 times the area of front panel 20, preferably the area of back panel 12 is 1.8 times the area of front panel 20. In an embodiment, the area of the bottom of the carton is from 4.1 to 4.5 times the area of top panel 34, preferably the area of the bottom of the carton 4.3 times the area of top panel 34.

Figure 2:
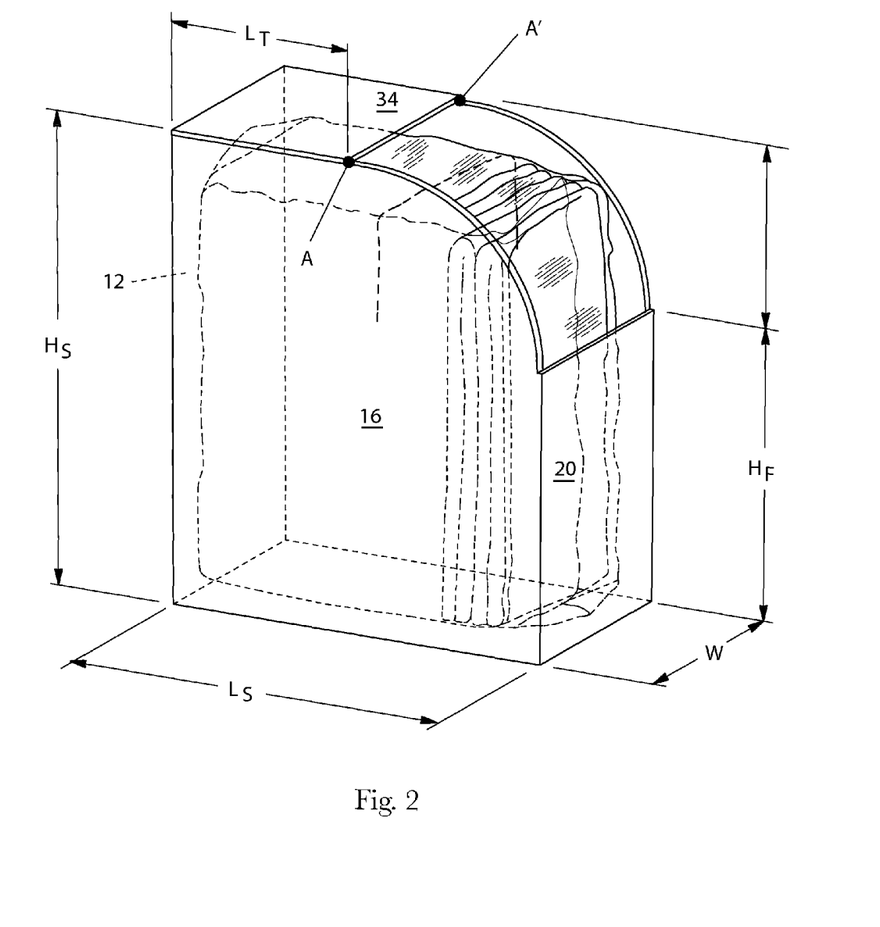
FIG. 2 is a perspective view of the carton loaded with absorbent articles arranged in a row and wrapped in a polybag.

As shown in FIG. 2, this carton is capable of containing absorbent articles, preferably in a row, preferably folded, more preferably folded in half about a latitudinal axis. In an embodiment, the absorbent articles are contained within a polybag, as shown in FIG. 2. In another embodiment (not shown), the absorbent articles are not contained within a polybag. Preferably the row is arranged so that it runs between front panel 20 and back panel 12, i.e. each absorbent article in the row is generally parallel to front panel 20 and back panel 12. The skilled person will appreciate that the number of absorbent articles comprising the row will depend at least on the thickness of each absorbent article and the depth of the carton. Where the absorbent articles are folded and placed in a row, adjacent articles may be arranged so that all the folded ends are facing in the same direction, either up or down, or be arranged so that the folded ends alternate in a predetermined pattern, e.g. every other one facing up, or other desired pattern. In an embodiment where all or substantially all of the folded ends face up, the row generally exhibits an inverted trapezoidal shape when observed from either of the sides of the row, such that the wider base of the trapezoid forms the top of the polybag and the narrower base of the trapezoid forms the bottom of the polybag. In this orientation, removal of the absorbent articles contained in the polybag is advantageously made easier after the tear line is torn, since the absorbent articles will naturally tend to push away from each other at the folded end to relieve the stress being placed on the front and back of the polybag due to the pressure on the polybag being greater at the top than at the bottom. Thus, as each successive absorbent article is removed from the polybag, the next absorbent article to be removed will require less exertion from the person removing it than the previously removed absorbent article.

It is believed that the placement and dimensions of the cut outs allow improved viewability of the absorbent articles. However, care has been taken balance the achievement of viewability with the need to retain a sufficient amount of and skillfully placed foldable material to give the carton enough structural integrity to be stacked during shipping, storing, and displaying without suffering deformation. For example, in an embodiment, front panel 20 is the single ply that comprises the front of the carton. However, as more strength is typically needed at the back of the carton, in an embodiment, the back of the carton comprises two plies, namely back panel 12 and back flap 28. As even more strength is typically need at the top of the carton, particularly in view of the cut outs, in an embodiment, the top of the carton comprise three plies, namely top panel 34, side end flap 38, and back end flap 30. These selections are believed to aide in improving the structural integrity of the carton.

During shipping, for example, a group of four cartons may be arranged where each of a pair of cartons have their back panels facing each other and the pairs are aligned such that the right hand side of one pair is adjacent to the left hand side of the other pair, thereby the tops of each of the cartons form, in essence, a single base to support the next higher row stacked similarly on top of them. Another advantage that the carton poses over conventional polybags in display, is that it clearly communicates to a stock person which end is the bottom and permits the stock person to stack multiple cartons, as described above or simply side by side where the row is one carton deep instead of more than one, thereby saving space in the store display, and at the same time presenting the consumer with an orderly display where the indicia on the carton and/or polybag contained within is easy to see and the absorbent articles are easy to see as well.

In forming blank 10 into a carton, back panel 12 and back flap 28 are adhered to each other, forming a sleeve. In this orientation, fold line 26 is preferably substantially flush with back edge 58. Back end flap 42 and front end flap 50 are folded in towards the sleeve such that they are substantially perpendicular to back panel 12 and front panel 20, respectively. Side end flap 46 and side end flap 54 are folded in towards the sleeve such that they are substantially perpendicular to side panel 16 and side panel 24, respectively, where notch 60 and notch 66 are engaged such that tab 62 overlaps tab 70 and tab 68 overlaps tab 64, or tab 62 is overlapped by tab 70 and tab 68 is overlapped by tab 64. Side end flap 46 and side end flap 54 are adhered to each other. The absorbent articles are loaded into the carton in a row, the absorbent articles preferably being arranged parallel to front panel 20 and back panel 12. In one embodiment, the absorbent articles are loaded directly into the carton. In another embodiment, the absorbent articles are wrapped in a polybag before being loaded into the carton. In yet another embodiment, the absorbent articles are wrapped in polybag 100 before being loaded into the carton. Back end flap 30 is folded in towards the sleeve such that it is substantially perpendicular to back panel 12. Side end flap 38 and top panel 34 are folded in towards the sleeve such that they are substantially perpendicular to side panel 24 and side panel 16, respectively. Side end flap 38 and top panel 34 are adhered to each other. In an embodiment where top panel 34 is provided with slot tab 72 and fold line 40 is provided with a corresponding slot 74, the carton may advantageously allow for top panel 34 to be recloseably fastened. In such an embodiment and other embodiments that allow top panel 34 to be recloseably fastened to side end flap 38, the row of absorbent articles may be replenished as used. This allows the carton to be re-used with more absorbent articles than originally packaged, which is desirable at least from an environmentally friendly standpoint. The various panels and flaps that are adhered to each other may be adhered to each other, e.g. by glue. A variety of hot melt adhesives are known in the art. This carton can also be constructed by taping, stapling and the like, or by locking, e.g. using slot tabs and slots. In yet another embodiment, the carton containing the absorbent articles is wrapped in a plastic film, e.g. shrink wrapped, after being fully assembled as described above.

When blank 10 is folded and various panels and flaps are adhered, the resulting carton has a partially closed end (exiting end) and a closed end. The absorbent articles exit the carton through the exiting end of the carton.

FIG. 2 shows the carton full of absorbent articles arranged in a row and wrapped in a polybag. In one embodiment, any polybag is used. In another embodiment, polybag 100, which comprises among other things, tear line 122, is advantageously used. As described above, it is also contemplated that in certain embodiments, the carton may be used without any polybag at all. It will be noted that the carton is a unitary structure and that the structural integrity of the carton is maintained by the fact that no portions of the carton are removed during shipping, storing, displaying, or dispensing. The structural integrity of the carton is improved by the fact that the back end flap 30, top panel 34, and side end flap 38 are made substantially coplanar with each other in formation of the carton, so as to provide a strong, weight accepting surface to form the top of the carton. This is accomplished while at the same time providing a cut-out area that spans portions of the top and front of the carton which allows for easy viewing of the carton's contents.

Figure 3:
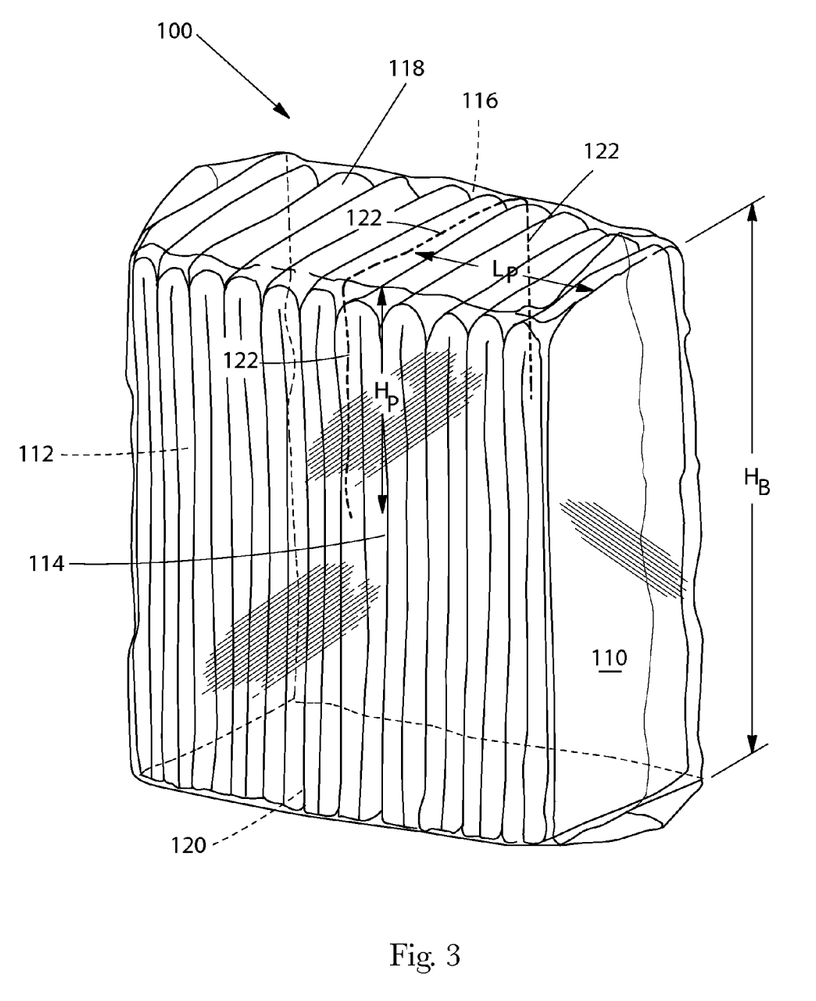
FIG. 3 is a perspective view of a polybag according to this invention wrapped around absorbent articles arranged in a row.

As described above, the absorbent articles may advantageously be wrapped in a polybag before being loaded into the carton. Referring to FIG. 3, a polybag 100 is provided that is formed around a row of absorbent articles by any method known in the art. This may include partially forming polybag 100, inserting the absorbent articles or wrapping the partially formed polybag around absorbent articles or a mixture thereof, and then closing the polybag around such absorbent articles, thereby containing them. Polybag 100 may comprise polyethylene, polypropylene, and combinations thereof. Polybag 100 may be single layered or a laminate having a plurality of layers. In an embodiment, polybag 100 comprises a polyethylene-polypropylene-polyethylene laminate. In those embodiments where polybag 100 comprises a laminate, the laminate may be co-extruded. Polybag 100 will typically have a thickness from 35 microns to 50 microns, preferably from 40 to 45 microns. In an embodiment where a thicker bag is desired, polybag 100 has a thickness from about 55 microns to about 65 microns.

Figure 4:
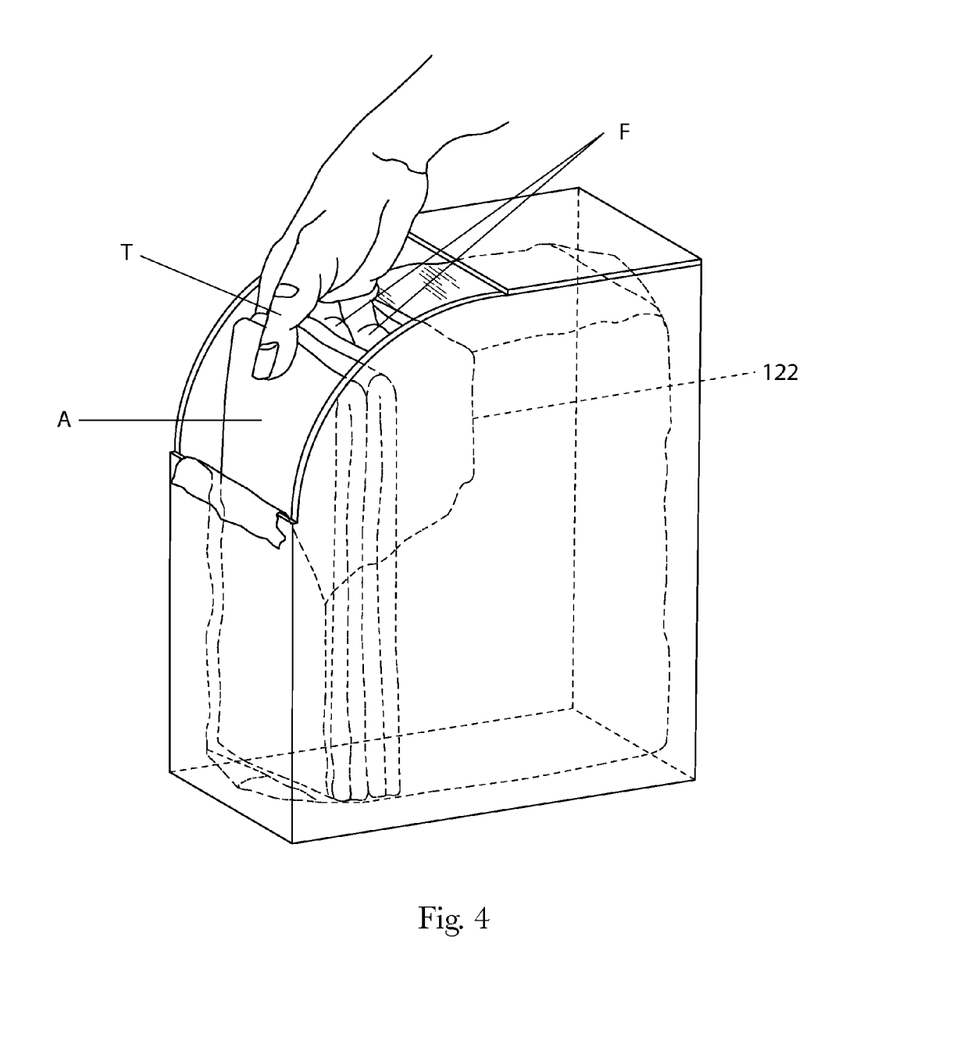
FIG. 4 is a perspective view of the carton containing a polybag that, in turn, contains absorbent articles, showing the polybag torn open at the tear line and an absorbent article being gripped by a hand for removal from the carton.

Polybag 100 will typically take on the general shape of the row of absorbent articles that it contains, as shown in FIG. 3. Still referring to FIG. 3, polybag 100 will typically have a front 110, a back 112, a side 114 and another side 116, a top 118 and a bottom 120. Seams may be formed at any suitable junction of the one or more plastic film sheets used to make polybag 100, using means known in the art, e.g. heat sealing or adhesive. Polybag 100 is provided with a tear line 122 that extends from and including a portion of side 114, across top 118, to and including a portion of side 116, of the polybag. The tear line may be formed by perforation, crimping, or other means known in the art, to provide a line that is weaker in structure as compared to the portions of polybag 100 adjacent to it, so as to facilitate opening the polybag by tearing apart the bag at tear line 122. In order to open the polybag, a person may insert fingers from one hand through the polybag at the tear line and then pull towards the front of the polybag to start the tearing of the polybag. Alternately, a person may insert fingers from each hand through the polybag at the tear line and then pull portions of the polybag away from each other by pulling their hands apart in opposite directions. In yet another alternative, a person may pinch portions of the polybag on either side of tear line 122, e.g. with the thumb and index finger from each hand pinching portions of the polybag on opposite sides of tear line 122, and then pull such portions of the polybag away from each other by pulling their hands apart in opposite directions. It will be noticed that tear line 122 is positioned along the a longitudinal axis, along Line R-R', of the row of absorbent articles and extends sufficiently into sides 114 and 116 such that when polybag 100 is opened by tearing along tear line 122, the opening created in polybag 100 sufficiently allows the absorbent articles contained therein to be retrieved by a consumer with their hands, as shown, e.g. in FIG. 4. As illustrated in FIG. 4, an absorbent article A can be easily removed from the carton by using the fingers F and the thumb T of a hand.

Tear line 122 is preferably positioned along the longitudinal axis such that is it located within 30 to 50% of the distance from the front of the polybag to the back of the polybag, i.e. length $L_P$ is $\geq 0.3 L_B$ and $\leq 0.5 L_B$. More preferably, tear line 122 is positioned along the longitudinal axis such that it is located within 35 to 45%, more preferably at 40%, of the distance from the front of the polybag to the back of the polybag, i.e. more preferably length $L_P$ is $\geq 0.35 L_B$ and $\leq 0.45 L_B$, more preferably length $L_P = 0.4 L_B$. Tear line 122 preferably runs across the top of the polybag and extends into sides 114 and 116 within 30 to 50% of the distance from the top of the polybag to the bottom, i.e. height $H_P$ is $\geq 0.3 H_B$ and $\leq 0.5 H_B$. More preferably, tear line 122 runs across the top of the polybag and extends into sides 114 and 116 within 35 to 45%, more preferably at 40%, of the distance from the top of the polybag to the bottom, i.e. more preferably height $H_P$ is $\geq 0.35 H_B$ and $\leq 0.45 H_B$, more preferably height $H_P = 0.4 H_B$. In an embodiment, tear line 122 extends into side 114 and 116 substantially the same distance.

To aid a consumer in locating tear line 122, it may be colored differently than the polybag, e.g. a clear polybag and a non-clear colored, e.g. blue, tear line, or otherwise differentiated to draw attention to it. In an embodiment where polybag 100 is used in a packaging system in conjunction with the carton assembled from blank 10, the carton may be provided with indicia that draws attention to tear line 122, e.g. an arrow or "tear here" statement printed on the carton that corresponds to the position of tear line 122. When used with such a carton, it will be noticed that tear line 122 is preferably positioned closer to the front of the carton than the edge of top panel 34 that is nearest the front of the carton, so that it is both visible and accessible to the consumer.

In an embodiment, polybag 100 contains a plurality of absorbent articles, where polybag 100 comprises: a front, a back, two sides, a top and a bottom, and a tear line extending from one side, across the top, to the other side of the polybag. In this embodiment, the absorbent articles are folded in half about a latitudinal axis and are arranged in a row that runs between the front and the back of the polybag, where the top of the polybag is the end to which the folded ends of the absorbent articles are facing. In another embodiment, polybag 100 also has indicia printed on each of the sides of the polybag, such that when the polybag is placed on its bottom with the top facing up, the indicia is oriented so that the indicia appears as upright. Such indicia may include words, e.g. brand name, size, product line, advertising, marketing claims, safety information, instructions for use, and the like, and/or graphics, e.g. pictures of users of the absorbent articles, caregivers, purchasers of the absorbent articles, advertising, and pictorial depictions of safety information and/or instructions for use, and the like.

In an embodiment where all or substantially all of the folded ends of the absorbent articles contained within polybag 100 face up, the length $L_X$ of the polybag at its top 118 is greater than the length $L_Y$ of the polybag at its bottom 120.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A blank for forming a partially closed carton for containing a plurality of absorbent articles, the blank comprising:
   a. a sheet of foldable material having first, second, and third parallel fold lines therein, defining areas of the sheet corresponding to a front, a side, a back, and another side of the carton;
   b. at one end of the parallel fold lines, a first fold line transverse to the parallel fold lines, a back end flap connected by the first transverse fold line to the area corresponding to the back, a top panel connected by the first transverse fold line to the area corresponding to one side, and a side end flap connected by the first transverse fold line to the area corresponding to the other side;
   c. at the other end of the parallel fold lines, a second fold line transverse to the parallel fold lines;
   d. a cut out of the portion of the sheet corresponding to the front of the carton such that substantially all of the area of the front panel that is within about 50% or less of the distance from the first transverse fold line to the second transverse fold line is cut away along a transverse cut line prior to forming the partially closed carton;
   e. substantially symmetrical cut outs of each of the portions of the sheet corresponding to the sides of the carton such that substantially all of the area of each side panel defined as follows is cut away prior to forming the partially closed carton:
      i. an arc originates at the point where the transverse cut line intersects the fold line that delineates the front from the respective side, and terminates at a point along the transverse line on the respective side;
      ii. the area on the side of the arc which is the portion of the respective side panel that is nearest the intersection of the fold line that delineates the front from the respective side and the transverse line is the portion to be cut away,
   wherein the top panel and the side end flap extend further away from the first transverse fold line than the back end flap, and
   wherein after forming the carton, the carton comprises a bottom opposite the top panel, wherein the area of the bottom of the carton is from about 4.1 to about 4.5 times the area of the top panel.

2. A blank according to claim 1, wherein a second back end flap is connected by the second transverse fold line to the area corresponding to the back, second side end flaps are connected by the second transverse fold line to each of the areas corresponding to the two sides, and a front end flap is connected by the second transverse fold line to the area corresponding to the front.

3. A blank according to claim 1, wherein the sheet has a fourth parallel fold line therein, defining an area of the sheet corresponding to a back flap of the carton.

4. A blank according to claim 3, wherein the area corresponding to one side comprises a first panel located between the first and second parallel fold lines, the area corresponding to the front comprises a second panel located between the second and third parallel fold lines, the area corresponding to the other side comprises a third panel located between the third and fourth parallel fold lines, and the area corresponding to the back comprises a back panel which is connected to the first panel at the first parallel fold line and a back flap which is connected to the third panel at the fourth parallel fold line.

5. A partially closed carton for containing a plurality of absorbent articles, the carton being formed from a blank according to claim 3.

6. A blank according to claim 4, wherein the distance from the first fold line to the second fold line and the distance from the third fold line to the fourth fold line are substantially equal.

7. A blank according to claim 4, wherein the distance that the top panel extends away from the first transverse fold line and the distance that the side end flap extends away from the first transverse fold line is substantially equal.

8. A blank according to claim 4, wherein the area of the back end flap that extends from the first transverse fold line, the area of the top panel that extends from the first transverse fold line, and the area of the side end flap that extends from the first transverse fold line, are substantially equal.

9. A blank according to claim 4, wherein the distance that each side end flap extends away from the second transverse fold line is substantially equal.

10. A blank according to claim 4, wherein the side panels of the carton substantially symmetrical about a vertical line of bisection drawn through the center of the front panel.

11. A blank according to claim 4, wherein the height of the side panels is greater than the length of the side panels.

12. A blank according to claim 4, wherein the height of the front panel is greater than or equal to about 0.5 times the height of the side panels.

13. A blank according to claim 12, wherein the height of the front panel is greater than or equal to about 0.55 times the height of the side panels.

14. A blank according to claim 13, wherein the height of the front panel is greater than or equal to about 0.6 times the height of the side panels.

15. A partially closed carton for containing a plurality of absorbent articles, the carton being formed from a blank according to claim 4.

16. A blank according to claim 1, wherein the area cut away to form the substantially symmetrical cut outs of each of the portions of the sheet corresponding to the sides of the carton is defined as follows for each side:
   i. the transverse cut line is virtually extended across the side;
   ii. a point on the transverse cut line is identified on the side, such point being equidistant from the fold line that delineates the front from the side, and from the transverse line;
   iii. the length from the fold line to the point defines a radius r;
   iv. using the point identified in item (ii) above, an arc having radius r is extended from the intersection of the transverse cut line and the fold line that delineates the front from the side, to the transverse line;
   v. the portion of the side panel on the side of the arc that is nearest the intersection of the fold line that delineates the front from the side, and the transverse line is the portion to be cut away.

17. A blank according to claim 1, wherein the origination point and termination point of the arc are equidistant from the point where the fold line that delineates the front from the respective side intersects the transverse line on the respective side.

18. A blank according to claim 1, wherein the cut out of the portion of the sheet corresponding to the front of the carton is provided such that substantially all of the area of the front panel that is within about 45% or less of the distance from the first transverse fold line to the second transverse fold line is cut away along a transverse cut line.

19. A blank according to claim 18, wherein the cut out of the portion of the sheet corresponding to the front of the carton is provided such that substantially all of the area of the front panel that is within about 40% or less of the distance from the first transverse fold line to the second transverse fold line is cut away along a transverse cut line.

20. A blank according to claim 1, wherein the area of the back panel is from about 1.6 to about 2 times the area of the front panel.

21. A blank according to claim 20, wherein the area of the back panel is about 1.8 times the area of the front panel.

22. A blank according to claim 1, wherein the area of the bottom of the carton is about 4.3 times the area of the top panel.

23. A partially closed carton for containing a plurality of absorbent articles, the carton being formed from a blank according to claim 1.

24. The blank according to claim 1, wherein upon formation of the blank into the partially closed carton, no portion of the carton is removed during shipping, storing, displaying or dispensing.

25. The blank according to claim 1, wherein upon formation of the blank into the partially closed carton, the back end flap, the top panel, and the side end flap overlap to form a top of the carton, wherein the top of the carton comprises three plies.

\* \* \* \* \*